United States Patent
Vélez Justiniano

(10) Patent No.: US 10,918,514 B2
(45) Date of Patent: Feb. 16, 2021

(54) TAMPER EVIDENT PACKAGING

(71) Applicant: Eric Vélez Justiniano, Northbrook, IL (US)

(72) Inventor: Eric Vélez Justiniano, Northbrook, IL (US)

(*) Notice: Subject to any disclaimer, the term of this patent is extended or adjusted under 35 U.S.C. 154(b) by 0 days.

(21) Appl. No.: 16/532,958

(22) Filed: Aug. 6, 2019

(65) Prior Publication Data
US 2020/0046546 A1  Feb. 13, 2020

Related U.S. Application Data

(60) Provisional application No. 62/717,861, filed on Aug. 12, 2018.

(51) Int. Cl.
| | | |
|---|---|---|
| *A61F 6/00* | (2006.01) | |
| *B65D 55/06* | (2006.01) | |
| *B65D 65/22* | (2006.01) | |
| *B65D 33/34* | (2006.01) | |
| *B65D 75/30* | (2006.01) | |

(52) U.S. Cl.
CPC .............. *A61F 6/005* (2013.01); *B65D 33/34* (2013.01); *B65D 55/06* (2013.01); *B65D 65/22* (2013.01); *B65D 75/30* (2013.01)

(58) Field of Classification Search
CPC .................. A61F 6/02; A61F 2006/043; A61F 2006/045; A61F 6/065; B65D 33/34; B65D 55/06; B65D 65/22; B65D 75/30
USPC ...... 206/69, 807; 220/592.01; 604/403, 404, 604/408, 410, 411, 415, 416
See application file for complete search history.

(56) References Cited

U.S. PATENT DOCUMENTS

| | | | |
|---|---|---|---|
| 4,434,893 A | | 3/1984 | Barlow |
| 4,511,052 A | | 4/1985 | Klein et al. |
| 4,653,643 A | | 3/1987 | Black |
| 4,813,541 A | | 3/1989 | Velasco et al. |
| 5,882,116 A | | 3/1999 | Backus |
| 7,882,838 B2 | | 2/2011 | Mallory |
| 2008/0210579 A1 | * | 9/2008 | Mallory ................. A61F 6/005 206/69 |
| 2009/0152133 A1 | * | 6/2009 | Felitsyn ................. A61F 6/005 206/69 |
| 2011/0056943 A1 | * | 3/2011 | Ueda .................... A61K 8/0212 220/266 |
| 2014/0332419 A1 | | 11/2014 | Gaines et al. |
| 2016/0137381 A1 | | 5/2016 | Gaines et al. |
| 2019/0071221 A1 | * | 3/2019 | Forman ................. B65D 33/20 |
| 2019/0152667 A1 | * | 5/2019 | Binder ................. B65D 75/327 |

* cited by examiner

*Primary Examiner* — Rafael A Ortiz
(74) *Attorney, Agent, or Firm* — James Conte; Conte Law Group

(57) ABSTRACT

A condom package has a first barrier having a first surface and an oppositely facing second surface. A second barrier of the package has a first and oppositely facing second surface. A first substance is between the first barrier first surface and second barrier second surface. A second substance and a condom are partitioned from the first substance and first barrier by the second barrier. The second substance and condom are in a bounded area delimited by the second barrier first surface.

20 Claims, 4 Drawing Sheets

- ▦ CHEMICAL B IN OUTER LAYER
- ▧ CHEMICAL A IN INNER LAYER
- ▬ CONDOM COATED BY CHEMICAL A OR C
- △ CHEMICAL C

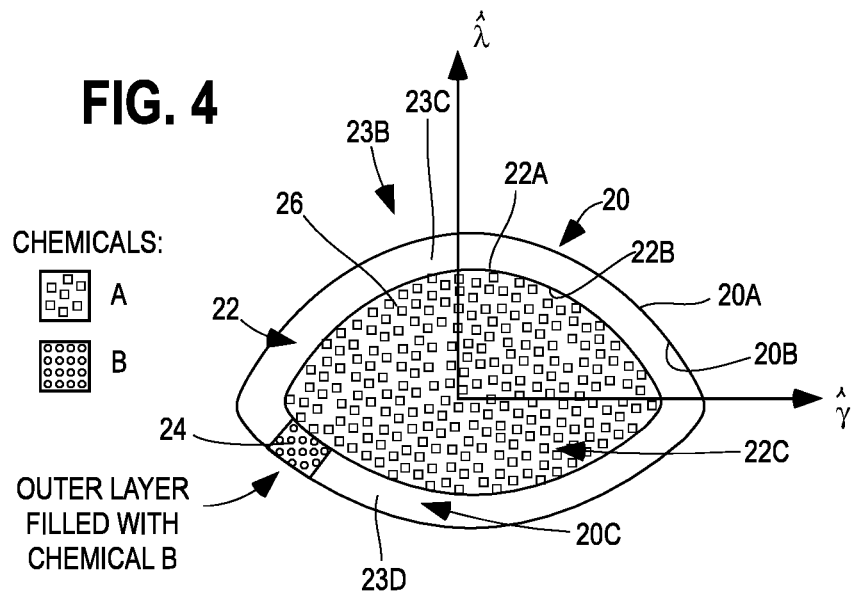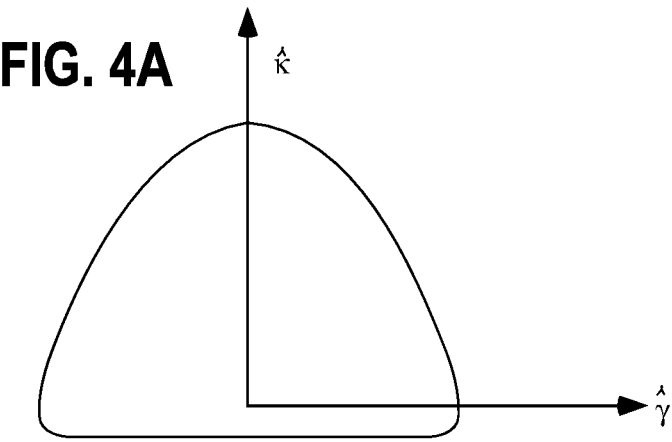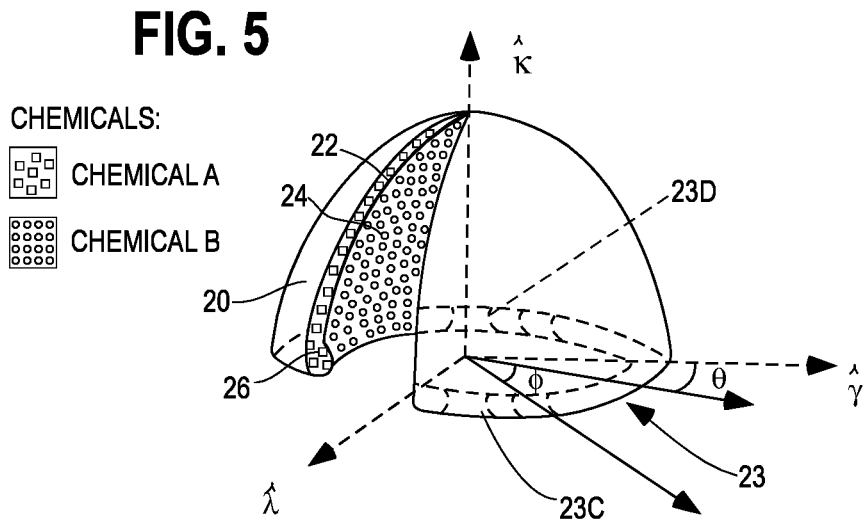

TAMPER EVIDENT PACKAGING

CROSS REFERENCE TO RELATED CASES

The present application claims the domestic priority benefit from U.S. provisional application 62/717,861, Eric Velez Justiniano, filed Aug. 12, 2018. The provisional application is incorporated herein into this application in its entirety by this reference.

FIELD

The present disclosure concerns a package wherein tampering with the packaging causes a chemical interaction between two substances of the packaging. The chemical interaction produces a plurality of touch detectible formations absent from the packaging prior to the interaction. The touch detectable formations comprise a plurality of touch detectable solid structures absent from the packaging prior to the interaction.

BACKGROUND

Different types of tamper evident packaging exist. U.S. Pat. No. 4,434,893, Tamper Evident Packaging, Barlow, discloses packaging which includes inner and outer gas-tight containers. The inner and outer containers are each pressurized with gas above atmospheric pressure to inflate their flexible walls. The capsules, pills and the like to be protected are located inside the inner container and the inner container is positioned inside the outer container providing a package which is difficult to tamper with and will clearly show evidence of tampering both through appearance and characteristic feel to the would-be purchaser.

U.S. Pat. No. 4,511,052, Container Seal with Tamper Evident Indicator, Klein, discloses a container assembly which incorporates a chemical indicator normally hermetically sealed from the ambient atmosphere, but exposed to the atmosphere upon opening of the container assembly. The indicator is adapted for changing appearance, either color or granule or crystal form, upon exposure to moisture or oxygen. The indicator is either located in the interior of a hermetically sealed container or is sealed in a frangible envelope which is operatively associated with a closure member of the container and is ruptured upon opening or attempted opening of the container.

U.S. Pat. No. 4,653,643, Tamper Evident Packaging, Black, discloses a package with contents enclosed within a first closed and sealed container. The first container is then enclosed within a second container, there being a void between the two containers. The second container includes a lid which is secured over its opening. Positioned between the lid and the opening of the second container is a permanently adhered thin sheet of elastic material or membrane which is impermeable to gas or liquid. This membrane is permanently adhered to the opening of the second container after the sealed first container and a portion of solid chemical material possessing the physical property of sublimation is placed into the void. In conjunction with the expansion into gas of the solid sublimation material at atmospheric pressure and normal ambient temperature subsequent to the permanent adhesion of the lid to the membrane and over the opening of the second container, the membrane stretches and expands outwardly from an aperture in the lid to produce visible and touchable positive evidence that the package has not been tampered with. The membrane is permanently destroyed when the lid is removed or when the membrane is punctured, cut or otherwise ruptured in any manner. This physical indicia remains intact for at least the shelf life of the article, unless tampering occurs. A transparent protective cover releasably connected over the lid is also provided.

U.S. Pat. No. 4,813,541, Tamper Proof Package, Velasco, discloses a hermetic multi-barrier tamperproof package for encasing articles such as pharmaceutical products and the like. The package comprises: a first container typically being made of a substantially impervious plastic material into which the articles to be protected are placed prior to hermetically sealing the container so as to enclose the articles, and so as to further enclose normal atmosphere air within the container. A second container typically being made of a substantially impervious plastic material completely encloses the first container. The first and second container are simultaneously separated from and connected to one another by attaching means comprising one or a number of discs having apertures in their centers, so as to allow a hermetic cavity defined between the first and second containers to extend continuously therebetween. A sensor comprising a select chemical or material is inserted within the cavity, and a select atmosphere such as a substantially evacuated atmosphere is simultaneously introduced within the cavity. The sensor and the select atmosphere co-operatively comprise a package integrity indicating sensor system where the sensor is simultaneously reactive to normal atmosphere air, and reversibly responsive to the presence or absence of the select atmosphere. A breach in package integrity will result in a loss of the select atmosphere and in exposure of the sensor to the normal atmosphere air enclosed within the first container and/or to the exterior atmosphere, whereby a chemical or physical response will occur that will produce an indication appealing to the sense of sight, touch, or smell at the point of puncture, or within the cavity that could evidence a package tampering. At least the first container incorporates a sealingly associated cap and body portions being provided with recloseable closure means. Alternatively, the select atmosphere is omitted and the sensor is sandwiched between and in contact with the outer surface of the first container and the inner surface of the second container. One or more barriers can be completely enclosing the second container, and at least one cavity can exist between the first container and an outermost barrier.

U.S. Pat. No. 5,882,116, Tamper Indicator Device, Backus, describes sheets composed of envelopes with generally thin cross sections containing compressed resilient cores which expand upon envelope breach. Expansion of the resilient core results in an obvious visual change to all or some of the envelope surfaces. Such envelopes may also contain a translucent liquid which greatly aids in amplifying the visual changes such envelopes may exhibit. Embodiments may take the form of applied labels, adhesive tape, wrapping paper, mail envelopes, bottle caps, document enclosures, blister packs, etc. Applications include not only signaling tampering but decorative and other applications as well. Processes for fabrication of embodiments are also described.

U.S. Pat. No. 7,882,838, Exothermic Condom Package, Mallory, discloses a condom package comprising a plurality of chambers, a first reactant disposed in a first chamber, a second reactant disposed in a second chamber, at least one breachable seal between the chambers with the reactants and a condom disposed in one of the chambers. The reactants are reactable to produce an exothermic reaction when in contact after the seal is breached. The package can have the condom in contact with at least one of the reactants prior to breaching the seal. Alternatively, the condom does not have contact with the reactants prior to breaching the seal. In addition, the condom does not have to have contact with the reactants even after the seal is breached. If the condom does not have contact with the reactants after the seal is broken, then the condom is preferably heated by thermal conduction through one or more walls of the plurality of chambers from the exothermic reaction of the reactants after the reactants are in contact with each other. The package can further comprise a flavoring agent and/or a lubricant disposed within at least one of the chambers.

US publication 2014/0332410, Damage Evident Condom, Gaines, discloses condom packaging having a damage indicating material applied between inner and outer wrapper layers. When the damage indicating material is exposed to oxygen, excessive heat and/or excessive pressure, the material changes in appearance to thereby alert the user that the condom package may be compromised. In US publication 2016/037381, Gaines, the damage indicating material may include an anti-counterfeiting taggant material.

SUMMARY

An example of the present invention includes a condom package that has a first barrier having a first surface and an oppositely facing second surface. A second barrier of the package has a first and oppositely facing second surface. A first substance is between the first barrier first surface and second barrier second surface. A second substance and a condom are partitioned from the first substance and first barrier by the second barrier. The second substance and condom are in a bounded area delimited by the second barrier first surface. Other features of the condom package are described below and shown in the drawings.

It is understood by those skilled in the art that items such as pills, drugs, medical devices or items which could replace and substitute for the condom which forms part of the package.

BRIEF DESCRIPTION OF THE DRAWINGS

FIG. 4 is a top view of the structure having the first and second barrier in an open position showing the first substance in the first bounded area and the second substance in the second bounded area; the condom has been omitted for simplicity.

FIG. 4A is a top view of the structure having the first and second barrier in an open position showing the first substance in the first bounded area and the second substance in the second bounded area; the condom has been omitted for simplicity.

FIG. 5 is a side view of the elements shown in FIG. 4 with a section of the elements removed.

Figure 1A:
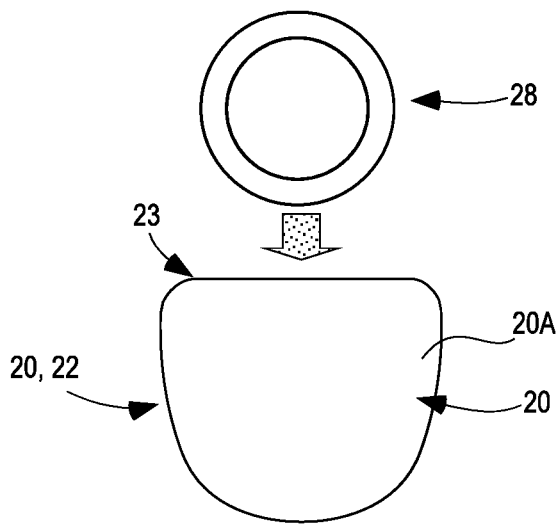
FIG. 1A is a view of a condom exploded from a structure having the first and second barrier embodying features of the present disclosure.
Figure 1B:
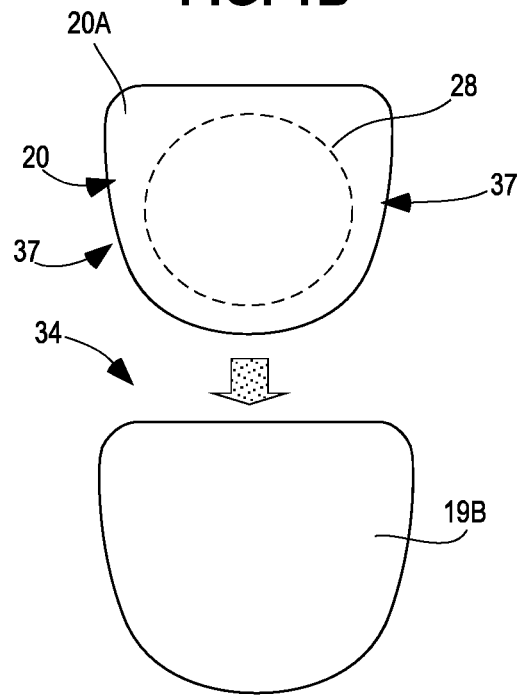
FIG. 1B is a view of the structure having the first and second barrier having the condom therein exploded from an open covering embodying features of the present invention.
Figure 2:
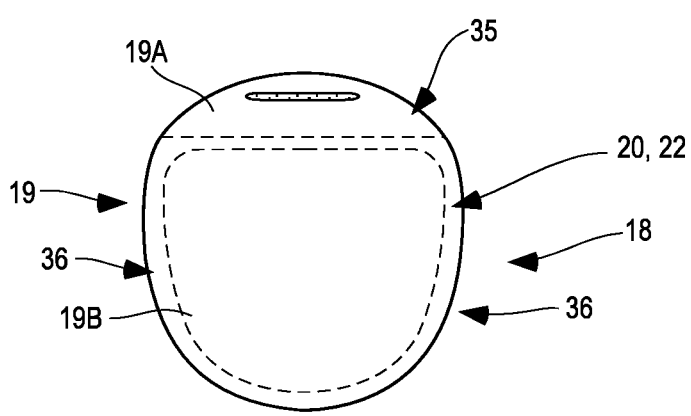
FIG. 2 is a face view of the packaging of the present disclosure showing the structure having the first and second barrier within the covering; the covering is closed, and the condom is not shown for simplicity.
Figure 3A:
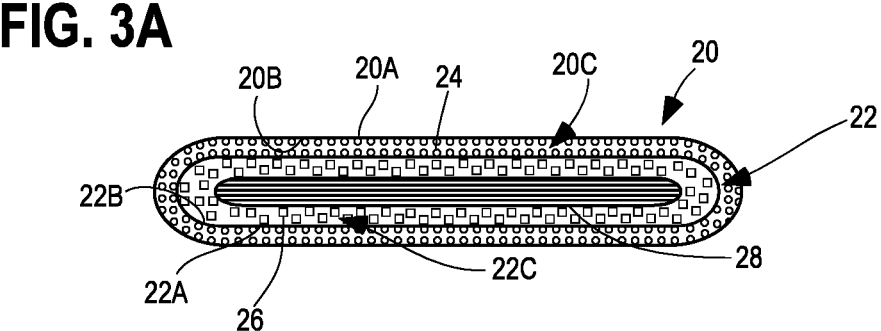
FIG. 3A is a sectional view of the of the structure with the first and second barrier having the condom therein shown in FIG. 1B; the section is taken along a laterally extending section line shown in FIG. 1B; the cross section shows a first substance in a first bounded area between the first and second barrier; a second substance in a second bounded area delimited by an internal surface of the second barrier; a condom is in the second bounded area.
Figure 3B:
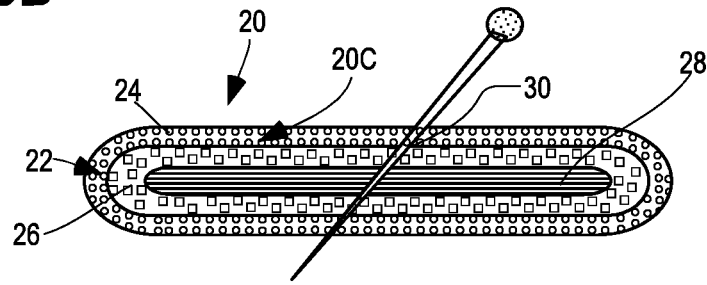
FIG. 3B is the sectional view shown in FIG. 3A with a pin piercing through the structure.
Figure 3C:
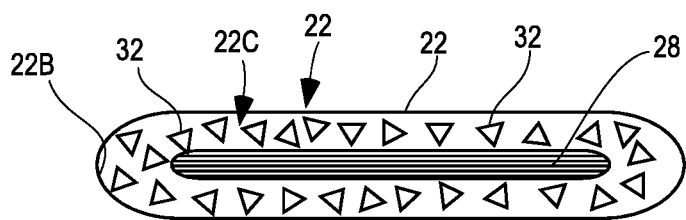
FIG. 3C is a view of the cross section shown in FIG. 3B absent the first barrier and pin; the first barrier has been ruptured by the pin pierce; the first substance has interacted with the second substance to form solid touch detectable formations in the second bounded area; the condom is present in the second bounded area.
Figure 6:
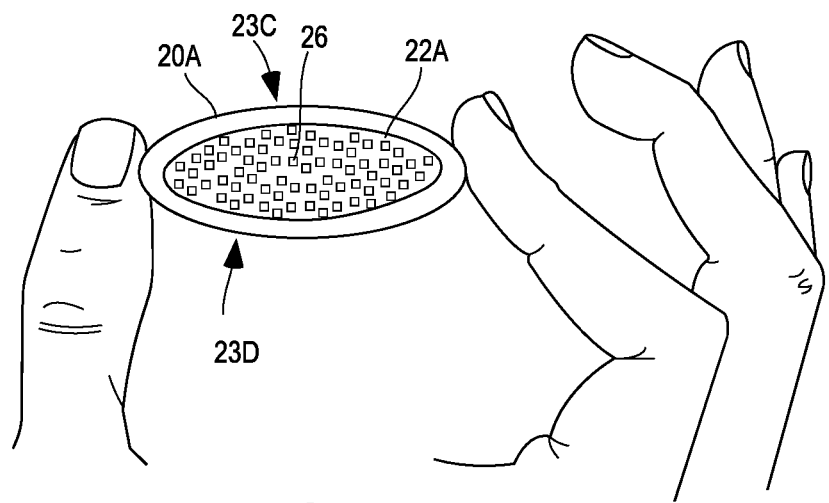
FIG. 6 is a top down view of the structure having the first and second barrier squeezed on its lateral sides to be in the open position, the condom and first substance have been omitted for simplicity.
Figure 7:
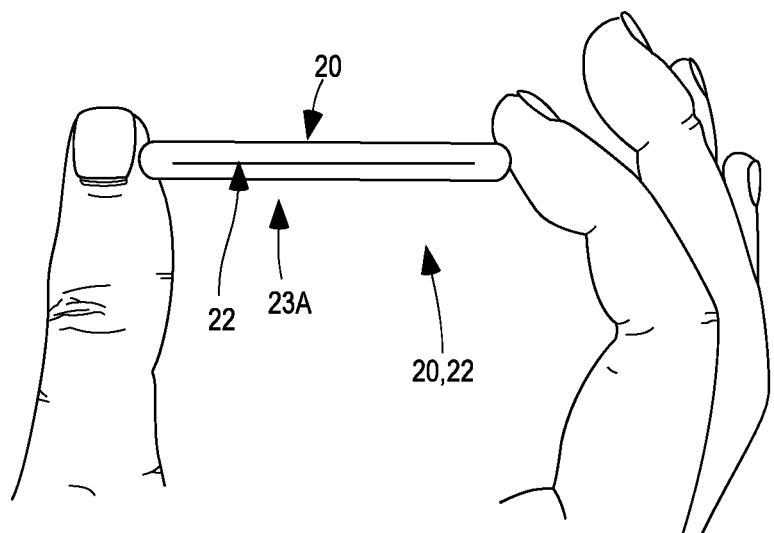
FIG. 7 is a top down view of the elements shown in FIG. 4 in the closed position.

Before any embodiments of the invention are explained in detail, it is to be understood that the invention is not limited in its application to the details of construction and arrangement of components set forth in the following description or as illustrated in the drawings. The invention is capable of other embodiments and of being practiced or of being carried out in various ways. Also, it is to be understood that the phraseology and terminology used herein is for description and should not be regarded as limiting. The use of "including," "comprising" or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

DETAILED DESCRIPTION

A condom package 18 includes a first barrier 20 and a second barrier 22. The first barrier has a second surface, external surface, 20a facing an external environment and a first surface, internal surface, 20b facing an environment internal to the first surface 20b of the first barrier 20. The internal environment includes a first substance 24, a second substance 26 and a condom 28. It also includes the second barrier 22. The second barrier has a first surface, internal surface, 22b and second surface, external surface, 22a. Within the internal environment the second barrier 22 partitions the second substance 26 from the first substance 24. The second barrier 22 seals off the second substance 26 from the first substance 24. The second barrier 22 also partitions the condom 28 from the first substance 24 and from the first barrier 20. The second barrier 22 seals off the condom 28 from the first substance 24 and first barrier 20. The second barrier internal surface 22b delimits a second bounded area 22c that has the second substance 26 and condom 28. The first substance 24 is between the external surface 22a of the second barrier 22 and the internal surface 20b of the first barrier 20. The first substance 24 is between the first barrier 20 and second barrier 22. The internal surface 20b of the first barrier 20 can delimit a first bounded area 20c. The external surface 22a of the second barrier 22a can also delimit part of the first bounded area 20c. The first bounded area 20c has the first substance 24. The first 20c and second 22c bounded areas are adjacent each other. The condom 28 is in contact with the second substance 26. When the second barrier 22 forming the second bounded area 22c has a tamper opening 30 therethrough, the first substance 24 interacts with the second substance 26, the interaction produces touch detectable formations 32 absent from the packaging 18 prior to the interaction. The interaction includes a chemical interaction and can include a chemical reaction. The phrase chemical interaction is broad enough to include the formation of ionic bonds. The opening therethrough 30 can comprise a break, puncture, tear, perforation, or piercing. The formations 32 are touch detectable structures which comprise at least atoms from the first and second substance. More particularly it includes the molecules of the second substance 26 ionically bonded to an atom of the first substance 24 such that the molecules of the first substance are cross linked. The touch detectable structures 32 have changed phase to solids. The solids 32 are squishable gel-like globules 32. At least some of the formations 32 are partitioned from the first barrier 20 by the second barrier 22 and in the second bounded area 22c. The first substance 24 is a salt solution. The second substance 26 is a polysaccharide solution or gel. The salt solutions are calcium chloride or potassium chloride solutions. The polysaccharide gel or solution is formed with sodium alginate and water. The solids are formed by the ionic bonding of sodium alginate molecules with the calcium or potassium of the salt.

Separation of a first portion 19a of an outer covering 19 from a second portion 19b of the covering 19 provides access 34. The access 34 is to the condom 28. The condom accessed is in the second bounded area 22c of the second barrier 22. The access 34 provides access to the condom 28 in the second bounded area 22c, without providing an opening for the first substance 24 to pass through and contact the second substance 26. A portion of the packaging 23 is manipulatable to close and open the second bounded area with the condom in the second bounded area. The covering 19 may have a tear line 35 or deformation to indicate and facilitate where the first portion 19a is separated from the second portion 19b. The first portion 19a may be a removable closure and the second portion 19b a container body coupled to the removable closure. The first portion 19a can be in sealed engagement with the second portion 19b. Separation of the first portion from 19a from the second portion 19b breaks the engagement.

A portion of the first barrier 20 can be coupled to a portion of the second barrier 22. The coupling may be seamless. The first 20 and second barrier 22 may be a double walled seamless container 20, 22 having a bowl like shape when open. The external surface 22a of the second barrier 22 and the internal surface 20b of the first barrier 20 can form the first bounded area 20c. The first bounded area 20c can be a compartment. The first bounded area 20c and first substance 24 are adjacent the second bounded area, which can be a compartment 22c, and adjacent the second substance 26 in the second bounded area 22c. When the second bounded area 22c is closed it is in the closed position 23a. When the second bounded area is open it is in the open position 23b. The second bounded area can be manipulated into having the open position 23b without allowing the first substance 24 to mix with the second substance 26 and without having to remove or detach the second barrier 22 from the first barrier 20.

The first barrier 20 and second barrier 22 can be removably attached or unattached to the covering 19 and removable through the access 34 from the covering 19. The first 20 and second 22 barrier once removed can be manipulated to place the second bounded area into the open position 23b from the closed position 23a to provide access to the condom 28. The first 20 and second barrier 22 do not have to be removed from the covering manipulate the second bounded area into the open position 23b. They can remain in the covering 19. The second barrier 22 can be manipulated into an open position 23b from the closed position with various constructions. For instance, a first portion 23c of the portion 23 manipulatable to open and close the second barrier can be separated from a second portion 23d of the portion 23 along a tear line or along a sealing engagement. Also, the portion 23 manipulatable to open and close the second bounded area 22c could be formed with a closure. Also, the portion manipulatable 23 to open and close the second bounded area 22c can be elastomeric. In the relaxed state, the portion manipulatable 23 closes the second bounded area. In the unrelaxed state, such as by being under a squeezing pressure by squeezing the lateral sides 37 of the first barrier 20 or squeezing the lateral sides 36 of the covering 19 with the first and second barrier therein, the manipulatable portion 23 oriented by the squeezing to place the second bounded 22c area in the open position 23b. If the second barrier 22 has a prior existing opening therethrough, a tamper opening 30, then touch detectable formations 32 will be present in the second bounded area 22c. A user when accessing the condom 28 will feel the touch detectable formations 32 as solids 32 and in particular solid globules as evidence of tampering and will know the condom package 18 has experienced tampering.

In further detail, the first barrier 20 and second barrier 22 form a double walled container 20, 22 which is normally closed with the condom in the second bounded area 22c when in the unopened covering 19. The closed container 20,22 has the internal 20b and external surface 20a of the first barrier 20. The first barrier 20 is a first wall. The internal surface 20b and external surface 22a delimit the first bounded area, compartment 20c, containing the first substance 24.

The second barrier 22 is a second wall of the closed double walled container 20, 22, excepting any tamper openings 30. It has the internal surface 22b delimiting the second bounded area 22c. Its external surface 22a contacts the first substance 24 and faces the internal surface 20b of the first wall. The second bounded area 22c has the second substance 26 and the condom 28. The double walled container 20, 22 is readily removeable by a user from the covering 19. To remove the container 20, 22 from the first covering 19, the covering 19 is opened. The first portion 19a of the covering is separated from the second portion 19b of the covering along tear line 35 or deformation to provide access 34 from which the container 20, 22 is removed. The container 20, 22 once removed is than oriented to the open position 23b by squeezing as described above. If a user feels touch detectable formations 32 in the second compartment container 22c, the user knows the condom package 18 has experienced a tampering.

The container 20, 22 does not have to be removed from the covering 19 after the first portion 19a is separated from the second portion 19b of the covering 19 to provide the access 34. The container portion 23 which opens and closes can be manipulated to the open position 23b from the closed position 23a while in the covering 19 by squeezing the lateral sides 36 of the covering 19.

The invention claimed is:
1. A condom package comprising:
a first barrier having a first surface and an oppositely facing second surface;
a first substance;

a second barrier, said second barrier having an first surface and an oppositely facing second surface and, the first surface of the first barrier faces the second surface of the second barrier, the second surface of the second barrier faces the first substance and said first substance is between the first surface of the first barrier and second surface of the second barrier;

a second substance and a condom are partitioned from the first substance and first barrier by the second barrier; and wherein when the second barrier has a tamper opening therethrough, the first substance interacts with the second substance, the interaction produces touch detectable formations absent from the packaging prior to the interaction.

2. The condom packaging of claim 1 comprising a first bounded area delimited with the first surface of the first barrier, said first bounded area having the first substance.

3. The condom packaging of claim 2 comprising a second bounded area delimited with the first surface of the second barrier, said second bounded area has the second substance and condom.

4. The condom packaging of claim 3 wherein the interaction of the first and second substance comprises a chemical interaction.

5. The condom packaging of claim 4 wherein the tamper opening comprises a break, puncture, tear, perforation or piercing.

6. The condom packaging of claim 5 wherein the formations, as part of the interaction, have changed phase into solids.

7. The condom packaging of claim 6 wherein the solids are globules.

8. The condom packaging of claim 3 wherein at least some of the formations are partitioned from the first barrier by the second barrier and are in the second bounded area.

9. The condom packaging of claim 1 wherein the first substance is a salt solution.

10. The condom packaging of claim 9 wherein the second substance is a polysaccharide solution or gel.

11. The condom packaging of claim 10 wherein the salt solution is a calcium chloride or potassium chloride solution and the polysaccharide gel or solution has sodium alginate and water.

12. The condom packaging of claim 3 wherein separation of a first portion of the packaging from a second portion of the packaging provides access to the condom contained in the second bounded area and said second barrier is in a closed position.

13. The condom packaging of claim 12 wherein the access leads to the condom contained in the second bounded area without causing an opening for the first substance to pass through the second barrier and contact the second substance.

14. The condom packaging of claim 12 wherein the first portion and the second portion of the packaging are formed from a covering.

15. The condom packaging of claim 3 wherein the first bounded area and first substance are adjacent the second bounded area and the second substance.

16. The condom packaging of claim 14 wherein a portion of the packaging is manipulatable from a closed position to an open position providing an opening into the second bounded area without allowing the first substance to mix with the second substance.

17. The condom packaging of claim 16 wherein the portion of the packaging manipulatable from the closed position to the open position is manipulatable while in a covering.

18. The condom packaging of claim 3 wherein when the second barrier has a tamper opening therethrough, the touch the detectable formations will be present in the second bounded area.

19. The condom packaging of claim 3 wherein the first barrier is a first wall of a double walled container.

20. The condom packaging of claim 3 wherein the second barrier is a second wall of a double walled container.

* * * * *